United States Patent [19]

Lewis et al.

[11] 4,228,286
[45] Oct. 14, 1980

[54] INTERMEDIATES FOR 11-[3-OXO-ω(2- AND 3-FURYL)-LOWER-ALKYL]HEXAHYDRO-2,6-METHANO-3-BENZAZOCINES

[75] Inventors: Thomas R. Lewis, Bethlehem; William F. Michne, Poestenkill, both of N.Y.

[73] Assignee: Sterling Drug Inc., New York, N.Y.

[21] Appl. No.: 71,744

[22] Filed: Aug. 30, 1979

Related U.S. Application Data

[60] Division of Ser. No. 36,060, May 4, 1979, which is a continuation-in-part of Ser. No. 886,781, Mar. 15, 1978, abandoned.

[51] Int. Cl.² .................... C07D 221/26; C07D 221/28
[52] U.S. Cl. ......................................... 546/97; 546/74
[58] Field of Search ................................. 546/97, 74

[56] References Cited

U.S. PATENT DOCUMENTS 3,250,678  5/1966  Archer ........................... 546/97 X
3,733,330  5/1973  Schubert et al. ..................... 546/97
3,776,914  12/1973  Atsumi et al. ........................ 546/97
3,932,422  1/1976  Michne .................................. 546/97

Primary Examiner—Henry R. Jiles
Assistant Examiner—Richard A. Schwartz
Attorney, Agent, or Firm—William G. Webb; B. Woodrow Wyatt

[57] ABSTRACT

3-$R_1$-6(eq)-$R_4$-7-$R_2''$-8-$R_2$-9-$R_2'$-10-$R_2'''$-11(ax)-$R_3$-11(eq)-[$CH_2CH_2CO(CH_2)_n$-(2- and 3-furyl)]-1,2,3,4,5,6-hexahydro-2,6-methano-3-benzazocines, useful as analgesics and narcotic antagonists, are prepared either by heating, with formic acid in an organic solvent or with certain ammonium formates, certain lower-alkyl 1-$R_1$-4aα-$R_3$-5α-$R_4$-6-$R_2''$-7-$R_2$-8-$R_2'$-9-$R_2'''$-3-[$CO(CH_2)_n$-(2- and 3-furyl)]-1,2,3,4,4 a,5,10,10a-octahydro-2,5-methanobenzo[g]quinoline-3-carboxylates or by reaction of a lower-alkyl β-[3-$R_1$-6-(eq)-$R_4$-7-$R_2''$-8-$R_2$-9-$R_2'$-10-$R_2'''$-11(ax)-$R_3$-1,2,3,4,5,6-hexahydro-2,6-methano-3-benzazocin-11(eq)-yl]propionate with 2 or 3-furylacetic acid in the presence of a strong base.

3 Claims, No Drawings

INTERMEDIATES FOR 11-[3-OXO-ω(2- AND 3-FURYL)-LOWER-ALKYL]HEXAHYDRO-2,6-METHANO-3-BENZAZOCINES

RELATED APPLICATIONS

This is a division of our prior, copending application Ser. No. 36,060, filed May 4, 1979, which in turn is a continuation-in-part of our prior application Ser. No. 886,781, filed March 15, 1978, abandoned May 4, 1979.

BACKGROUND OF THE INVENTION

1. Field of the Invention

This invention relates to 3-$R_1$-6(eq)-$R_4$-7-$R_2''$-8-$R_2$-9-$R_2'$-10-$R_2'''$-11(ax)-$R_3$-11(eq)-[$CH_2CH_2CO(CH_2)_n$-(2- and 3-furyl)]-1,2,3,4,5,6-hexahydro-2,6-methano-3-benzazocines, useful as analgesics and narcotic antagonists.

2. Description of the Prior Art

Michne, U.S. Pat. No. 3,932,422, patented Jan. 13, 1976, describes certain 1,2,3,4,5,6-hexahydro-2,6-methano-3-benzazocines having an 11(eq)-alkyl side chain bearing ketone or carbinol functions; and other art, for example Archer U.S. Pat. No. 3,250,678, patented May 10, 1966, describes 1,2,3,4,5,6-hexahydro-2,6-methano-3-benzazocines having unsubstituted lower-alkyl groups at the 11-position, for example methyl or ethyl. However, such 1,2,3,4,5,6-hexahydro-2,6-methano-3-benzazocines having an 11-alkyl side chain substituted with other functional groups, for example heterocyclic groups such as furyl, are unknown in the prior art.

SUMMARY OF THE INVENTION

In a composition of matter aspect, the present invention relates to certain 3-$R_1$-6(eq)-$R_4$-7-$R_2''$-8-$R_2$-9-$R_2'$-10-$R_2'''$-11(ax)-$R_3$-11(eq)-[$CH_2CH_2CO(CH_2)_n$-(2-and 3-furyl)]-1,2,3,4,5,6-hexahydro-2,6-methano-3-benzazocines, which are useful as analgesics and narcotic antagonists.

DETAILED DESCRIPTION INCLUSIVE OF THE PREFERRED EMBODIMENTS

More specifically, this invention provides compounds having the formula

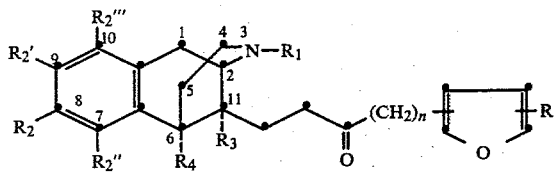

and chemically designated 3-$R_1$-6(eq)-$R_4$-7-$R_2''$-8-$R_2$-9-$R_2'$-10-$R_2'''$-11(ax)-$R_3$-11(eq)-[$CH_2CH_2CO(CH_2)_n$-(2- and 3-furyl)]-1,2,3,4,5,6-hexahydro-2,6-methano-3-benzazocines, which are useful as analgesics and narcotic antagonists, and wherein R is hydrogen or lower-alkyl; $R_1$ is hydrogen, lower-alkyl, cyclo-lower-alkyl-lower-alkyl, phenyl-lower-alkyl, lower-alkenyl or lower-alkynyl; $R_2$, $R_2'$, $R_2''$ and $R_2'''$ are each hydrogen, or three of them are hydrogen and the fourth is hydroxy, methoxymethoxy, lower-alkoxy or 2-tetrahydropyranyloxy; $R_3$ and $R_4$ are each hydrogen or lower-alkyl, or $R_3$ and $R_4$ together are divalent lower-alkylene, -$(CH_2)_m$-, where m is one of the integers 3 and 4; and n is 0 (zero) or the integers 1 or 2.

As used herein, the terms lower-alkyl and lower-alkoxy mean saturated, acyclic groups which may be straight or branched containing from one to about seven carbon atoms as exemplified by methyl, ethyl, propyl, isopropyl, butyl, methoxy, ethoxy, propoxy, isopropoxy or butoxy.

As used herein, the erms lower-alkenyl and lower-alkynyl mean monovalent groups of from three to seven carbon atoms containing one double or triple bond as illustrated, for example, by 1-propenyl, 2-butenyl, 4-pentenyl, 3-methyl-2-butenyl, 1-methyl-2-propenyl, 2-methyl-2-propenyl, 2-propynyl, 2-butynyl, 4-pentynyl, 2-hexynyl and the like.

As used herein, the term cyclo-lower-alkyl means saturated carbocyclic groups containing from three to seven ring carbon atoms as illustrated, for example, by cyclopropyl, cyclobutyl, cyclopentyl, cyclohexyl, 2-methylcyclobutyl, 4-ethylcyclohexyl and the like.

The compounds of formula I where n is 0 or the integer 2 are prepared by heating a lower-alkyl 1-$R_1$-4α-$R_3$-5α-$R_4$-6-$R_2'$-7-$R_2$-8-$R_2'$-9-$R_2'''$-3-[$CO(CH_2)_n$-(2- or 3-furyl)]-1,2,3,4,4a,5,10,10a-octahydro-2,5-methanobenzo[g]-quinoline-3-carboxylate having the formula

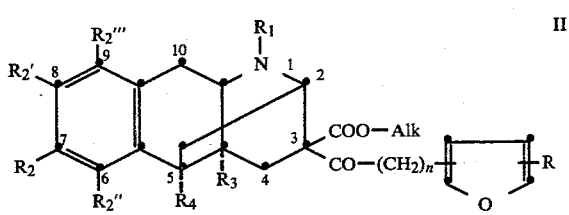

where R, $R_1$, $R_2$, $R_2'$, $R_2''$ $R_2'''$, $R_3$, $R_4$ and n have the meanings given above, and Alk is lower-alkyl, with formic acid in an inert organic solvent at a temperature from 100°–150° C. or with a benzyl-di-lower-alkylammonium formate or a tri-lower-alkylammonium formate at a temperature in the range from 120°–150° C. The reaction results in ring opening between the 2- and 3-ring carbon atoms of the compounds of formula II followed by decarbalkoxylation of the 3-carbo-lower-alkoxy group, COO-Alk. Suitable solvents are toluene, xylene or mesitylene. A preferred reaction medium is formic acid in mesitylene. A particularly preferred method involves ring opening in trimethylammonium formate.

The compounds of formula I where n is one of the integers 1 and 2 are prepared by reacting a 2- or 3-furylacetic acid or a β-(2- or 3-furylpropionic)acid halide, in the presence of two molar equivalents of an alkali metal amide, with a compound having the formula

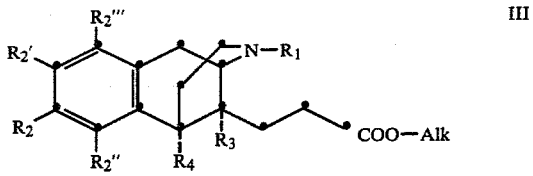

where $R_1$, $R_2$, $R_2'$, $R_2''$, $R_2'''$, $R_3$, $R_4$ and Alk have the meanings given above, followed by decarbalkoxylation of the resulting β-keto ester having the formula

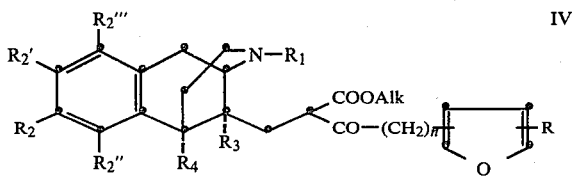

where R, $R_1$, $R_2$, $R_2'$, $R_2''$, $R_2'''$, $R_3$, $R_4$, Alk and n have the meanings given above, in formic acid in mesitylene, or trimethylammonium formate using the same conditions as described above for the simultaneous ring opening and decarbalkoxylation of the compounds of formula II. The acylation reaction is carried out in an inert organic solvent, for example dioxane or tetrahydrofuran. Suitable alkali metal amides are sodamide or lithium di-lower-alkylamides, such as lithium diisopropylamide.

The compounds of formula I where one of $R_2$, $R_2'$, $R_2''$ and $R_2'''$ is methoxymethoxy are prepared by reaction of the corresponding compounds where the corresponding group is hydroxy with dimethoxymethane in the presence of a catalytic amount of a strong acid and in an inert organic solvent. The reaction is carried out by refluxing a solution of the reactants in the chosen solvent, for example chloroform, methylene dichloride, ethylene dichloride and the like, under a Soxhlet extractor containing molecular sieves having a pore size sufficient to trap and hold molecules of methanol. In this way the methanol produced in the reversible reaction is removed from the reaction mixture as it is formed, and the reaction proceeds to completion. It has been found that 4A molecular sieves have a porosity of the proper size for this purpose.

The compounds of formula I where one of $R_2$, $R_2'$, $R_2''$ and $R_2'''$ is methoxymethoxy are particularly useful as intermediates for preparing the corresponding compounds where the corresponding group is hydroxy and which contain acid sensitive groups elsewhere in the molecule, for example compounds where $R_1$ is cyclo-lower-alkyl-lower-alkyl where cyclo-lower-alkyl is cyclopropyl, since the methoxymethoxy group is readily cleaved under mild acid conditions. In fact an alternative method for preparing the compounds of formula I where one of $R_2$, $R_2'$, $R_2''$ and $R_2'''$ is hydroxy comprises heating a compound of formula II or a β-keto ester of formula IV resulting from acylation of a compound of formula III, where in either case one of $R_2$, $R_2'$, $R_2''$ and $R_2'''$ is methoxymethoxy, with formic acid in an inert organic solvent or with a benzyl-di-lower-alkylammonium formate or a tri-lower-alkylammonium formate as described above. The conditions of the reaction are sufficiently acidic to effect not only ring opening of the compounds of formula II or decarbalkoxylation of the β-keto ester of formula IV to produce the compounds of formula I but also to effect cleavage of the methoxymethoxy group to the hydroxy group.

The compound of formula II where one of $R_2$, $R_2'$, $R_2''$ and $R_2'''$ is methoxymethoxy are prepared from the corresponding compounds where the corresponding group is hydroxy in the same manner described above with respect to the preparation of the compounds of formula I where one of the subject groups is methoxymethoxy.

The compounds of formula I where $R_1$ is benzyl can be catalytically debenzylated to give the corresponding compounds where $R_1$ is hydrogen. The latter can then be realkylated with an appropriate alkylating agent to give other different compounds where $R_1$ has the meanings, other than hydrogen, given above. Reduction is carried out in an inert organic solvent, for example ethanol, isopropanol and the like, and at pressures from 40 to 100 p.s.i.g. A preferred catalyst is palladium-on-charcoal. The alkylation of the compounds of formula I where $R_1$ is hydrogen is carried out in an inert organic solvent, for example acetone, ethanol or dimethylformamide (hereinafter DMF), and in the presence of an acid-acceptor, for example alkali metal carbonates or bicarbonates.

The compounds of formula I where $R_1$ is benzyl are thus useful as intermediates for the preparation of other compounds of formula I where $R_1$ has the other different meanings given above.

The compounds of formula I where $R_1$ is lower-alkenyl, lower-alkynyl, cyclo-lower-alkyl-lower-alkyl or phenyl-lower-alkyl (e.g. phenylethyl) are advantageously prepared from the corresponding compounds where $R_1$ is hydrogen by reaction of the latter with an appropriate lower-alkenyl halide, lower-alkynyl halide, cyclo-lower-alkyl-lower-alkyl halide or phenyl-lower-alkyl halide, as the case may be, in an inert organic solvent, for example a lower-alkanol, acetone or DMF, in the presence of an acid-acceptor, for example an alkali metal carbonate or bicarbonate. A preferred solvent is DMF.

The compounds of formulas II and III and the methods for their preparation are disclosed in our U.S. Pat. No. 4,119,628, patented Oct. 10, 1978, and continuation-in-part application thereof Ser. No. 878,308, filed Feb. 16, 1978, now U.S. Pat. No. 4,148,749, patented Apr. 10, 1979, the disclosures of which are incorporated herein by reference.

Due to the presence of a basic amino grouping, the free base forms represented by formula I above react with organic and inorganic acids to form acid-addition salts. The acid-addition salt forms are prepared from any organic or inorganic acid. They are obtained in conventional fashion, for instance either by direct mixing of the base with the acid or, when this is not appropriate, by dissolving either or both of the base and the acid separately in water or an organic solvent and mixing the two solutions, or by dissolving both the base and the acid together in a solvent. The resulting acid-addition salt is isolated by filtration, if it is insoluble in the reaction medium, or by evaporation of the reaction medium to leave the acid-addition salt as a residue. The acid moieties or anions in these salt forms are in themselves neither novel nor critical and therefore can be any acid anion or acid-like substance capable of salt formation with the base.

Representative acids for the formation of the acid-addition salts include formic acid, acetic acid, isobutyric acid, alpha-mercaptopropionic acid, trifluoroacetic acid, malic acid, fumaric acid, succinic acid, succinamic acid, tannic acid, glutamic acid, tartaric acid, oxalic acid, pyromucic acid, citric acid, lactic acid, glycolic acid, gluconic acid, saccharic acid, ascorbic acid, penicillin, benzoic acid, phthalic acid, salicylic acid, 3,5-dinitrobenzoic acid, anthranilic acid, cholic acid, 2-pyridinecarboxylic acid, pamoic acid, 3-hydroxy-2-naphthoic acid, picric acid, quinic acid, tropic acid, 3-indoleacetic acid, barbituric acid, sulfamic acid, methanesulfonic acid, ethanesulfonic acid, isethionic acid, benzenesulfonic acid, p-toluenesulfonic acid, butylarsonic acid, methanephosphonic acid, acidic resins, hydrofluoric acid, hydrochloric acid, hydrobromic acid, hydriodic acid, perchloric acid, nitric acid, sulfuric acid, phosphoric acid, arsenic acid and the like.

All of the acid-addition salts are useful as sources of the free base forms, by reaction with an inorganic base. It will thus be appreciated that if one or more of the characteristics, such as solubility, molecular weight, physical appearance, toxicity, or the like of a given base or acid-addition salt thereof render that form unsuitable for the purpose at hand, it can be readily converted to another, more suitable form. For pharmaceutical purposes, acid-addition salts of relatively non-toxic, pharmaceutically-acceptable acids, for example hydrochloric acid, lactic acid, tartaric acid, and the like, are of course employed.

The compounds of this invention can exist in enantiomeric forms separable into enantiomers. If desired, the isolation or the production of a particular enantiomeric form can be accomplished by application of general principles known in the prior art. In the nomenclature employed for the compounds of formula I herein, "ax" stands for axial and "eq" for equatorial, and the configurations are given with reference to the hydroaromatic ring. Thus, the 6(eq), 11(ax) compounds of formula I are in the cis configuration, whereas the 6(eq), 11(eq) compounds are in the trans configuration.

In the nomenclature employed for the compounds of formula II, again configurations are given with reference to the hydroaromatic ring, and the designation "β" indicates the cis configuration relative to the 2,5-methano bridge of the compounds of formula II. Conversely, the designation "α" indicates the trans configuration relative to the same groups.

In standard pharmacological test procedures, the compounds of formula I and the acid-addition salts thereof have been found useful as depressants of the central nervous system, and more particularly have been found useful as analgesics and as antagonists of strong analgesics such as phenazocine, meperidine and morphine.

The compounds of formula I can be administered in the same manner as known analgesics and antagonists of strong analgesics, i.e. parenterally or orally in any of the conventional pharmaceutical forms, as for instance solutions, suspensions, tablets, capsules and the like.

As described above and as will be seen hereinbelow, many of the species of formula I are readily interconvertible by simple and well-known reactions such as ether cleavage, etherification and the like, so that they are also useful as intermediates for each other.

The useful properties of the compounds of this invention were demonstrated by standard pharmacological procedures readily carried out by technicians having ordinary skill in pharmacological test procedures, so that the actual determination of the numerical biological data definitive for a particular test compound can be ascertained without the need for any extensive experimentation.

The test procedures used to determine the analgesic and analgesic antagonist activities of the compounds of the invention have been described in detail in the prior art and are as follows: the acetylcholine-induced abdominal constriction test, which is a primary analgesic screening test designed to measure the ability of a test agent to suppress acetylcholine-induced abdominal constriction in mice, described by Collier et al., Brit. J. Pharmacol. Chemotherap. 32, 295 (1968); a modification of the anti-bradykinin test, which is also a primary analgesic screening procedure, described by Berkowitz et al., J. Pharmacol. Exp. Therap. 177, 500–508 (1971), Blane et al., J. Pharm. Pharmacol. 19, 367–373 (1967), Botha et al., Eur. J. Pharmacol. 6, 312–321 (1969) and Deffenu et al., J. Pharm. Pharmacol. 18, 135 (1966); the phenyl-p-quinone-induced writhing test, also a primary analgestic screening test, designed to measure the ability of a test agent to prevent phenyl-p-quinone-induced writhing in mice, described by Pearl and Harris, J. Pharmacol. Exptl. Therap. 154, 319–323 (1966); the rat tail flick radiant thermal heat analgesic (agonist) test described by D'Amour and Smith, J. Pharmacol. Exptl. Therap. 72, 74 (1941) as modified by Bass and Vanderbrook, J. Am. Pharm. Assoc. Sci. Ed. 41, 569 (1956); the phenazocine antagonist test, which is designed to measure the ability of a test agent to antagonize the effect of phenazocine in the above-indicated rat tail flick response test, described by Harris and Pierson. J. Pharmacol. Exptl. Therap. 143, 141 (1964); and the Straub tail test which is an observation of erection and arching of the tail in mice and which is characteristic of narcotic analgesics, such as morphine, first described by Straub, Dtsch. med. Wochr. (1911), page 1426 and further described by Aceto et al., Brit. J. Pharmacol. 36, 225–239 (1969).

The structures of the compounds of this invention were established by the modes of synthesis, by elementary analyses and by ultraviolet, infrared and nuclear magnetic resonance spectra. The course of reactions and homogeneity of the products were ascertained by thin layer chromatography.

The manner and process of making and using the invention, and the best mode contemplated by the inventors of carrying out this invention, will now be described so as to enable any person skilled in the art to which it pertains to make and use the same. The melting points are uncorrected.

EXAMPLE 1

A solution of 20.5 g. (0.04 mole) of ethyl 1,4aα,5α-trimethyl-7-methoxy-3-(2-furoyl)-1,2,3,4,4a,5,10,10a-octahydro-2,5-methanobenzo[g]quinoline-3-carboxylate in 60 ml. of trimethylammonium formate was heated under reflux for twelve minutes, then cooled, mixed with ice water and rendered basic by the addition of excess sodium hydroxide. The mixture was extracted twice with ether, and the extracts were washed with brine, dried over magnesium sulfate and taken to dryness to give 18.5 g. of an oil. The latter was dissolved in 150 ml. of 95% ethanol, the mixture rendered alkaline by the addition of a solution containing 1 g. of potassium hydroxide in 20 ml. of water, allowed to stand for twenty-four hours, refluxed for four hours, then taken to dryness, and the residue extracted with diethyl ether. The combined ether extracts, on washing with water, drying over magnesium sulfate and evaporation to dryness, afforded 26 g. of an oil which, on trituration with hexane, afforded solid material which was collected and recrystallized from acetone to give 4.3 g. of 3,6(eq),1-1(ax)-trimethyl-8-methoxy-11(eq)-[3-oxo-3-(2-furyl)-propyl]-1,2,3,4,5,6-hexahydro-2,6-methano-3-benzazocine, m.p. 119°–122° C.

EXAMPLE 2

A solution of 33.3 g. (0.08 mole) of diethyl 1,4aα,5α-trimethyl-7-methoxy-1,2,3,4,4a,5,10,10a-octahydro-2,5-methanobenzo[g]quinoline-3,3-dicarboxylate in 100 ml.

of trimethylammonium formate was refluxed for fifteen minutes, then concentrated in vacuo. The residue was poured onto ice, the mixture basified with excess 10% sodium hydroxide and extracted with methylene dichloride. The organic extracts, on washing with water and concentration to an oil, afforded 29.7 g. of crude product, consisting of ethyl β-[3,6(eq),11(ax)-trimethyl-8-methoxy-1,2,3,4,5,6-hexahydro-2,6-methano-3-benzazocin-11(eq)-yl]propionate, which gradually solidified. The latter was mixed with 200 ml. of 48% hydrobromic acid and refluxed for one hour. The mixture, on concentration to a smaller volume, afforded a solid which was collected and dried to give crude β-[3,6(eq),11(ax)-trimethyl-8-hydroxy-1,2,3,4,5,6-hexahydro-2,6-methano-3-benzazocin-11(eq)-yl]propionic acid.

The latter (14.8 g., 0.046 mole) was suspended in 400 ml. of absolute ethanol, the mixture was saturated with gaseous hydrogen chloride and allowed to stand at ambient temperature. The resulting clear solution was concentrated to a small volume to give a white solid which was suspended in water and sufficient saturated sodium bicarbonate to give a pH of 7–8. The resulting mixture was extracted with methylene dichloride, and the organic extracts were dried over anhydrous magnesium sulfate and taken to dryness. The resulting residue, about 17 g., was dissolved in 70 ml. of acetone and the solution treated with 5.6 g. of ethanesulfonic acid. The solution was diluted slightly with diethyl ether, and the resulting solid which separated was collected and dried to give 16.5 g. of ethyl β-[3,6(eq),11(ax)-trimethyl-8-hydroxy-1,2,3,4,5,6-hexahydro-2,6-methano-3-benzazocin-11(eq)-yl]propionate ethanesulfonate, m.p. 235°–238° C.

The latter (4.2 g., 0.009 mole) was dissolved in 15 ml. of dimethylformamide, the solution treated with three drops of ethanesulfonic acid and then with 15 ml. of 2,3-dihydropyran and stirred for forty-five minutes at 75°–80° C. The mixture was then poured into 100 ml. of cold 5% sodium hydroxide and quickly extracted with diethyl ether. The ether extracts, on washing with dilute sodium hydroxide, drying over magnesium sulfate and evaporation to dryness afforded 5 g. of ethyl β-[3,6(eq),11(ax)-trimethyl-8-[2-(tetrahydropyranyloxy)]-1,2,3,4,5,6-hexahydro-2,6-methano-3-benzazocin-11(eq)-yl]propionate as an oil.

A solution of 0.04 mole of lithium diisopropylamide was prepared by addition of 4.0 g. (0.04 mole) of diisopropylamine to a solution of 21 ml. (0.04 mole) of a 1.9 molar hexane solution of butyl lithium in 40 ml. of tetrahydrofuran. The solution was then treated, over a period of fifteen minutes, with a solution of 2.5 g. (0.02 mole) of 2-furylacetic acid in 60 ml. of tetrahydrofuran. A solution of 3.9 g. of the above described 8-(tetrahydropyranyloxy)ether in 30 ml. of tetrahydrofuran was then added over a period of fifteen minutes with stirring. The mixture was stirred at ambient temperature for three hours, cooled and treated with 90 ml. of a 1 N solution of hydrochloric acid. The mixture was then heated to 50° C., the solvent removed in vacuo and the residue poured into ice water and the mixture basified by addition of saturated sodium bicarbonate. Extraction of the mixture with methylene dichloride, washing the extracts with water, drying over magnesium sulfate and evaporation to dryness afforded 4.2 g. of a red oil which was extracted with hexane. The hexane extracts, on evaporation to dryness, afforded 1.8 g. of an oil which was dissolved in ethanol and treated with a solution of ethereal hydrogen chloride to give 1.4 g. of 3,6(eq),1-1(ax)-trimethyl-8-hydroxy-11(eq)[3-oxo-4-(2-furyl)-butyl]-1,2,3,4,5,6-hexahydro-2,6-methano-3-benzazocine hydrochloride, m.p. 279°–281° C.

EXAMPLE 3

A solution of 14.2 g. (0.035 mole) of ethyl 1,4aα,5α-trimethyl-3-(2-furoyl)-1,2,3,4,4a,5,10,10a-octahydro-2,5-methanobenzo[g]quinoline-3-carboxylate in a solution of 142 ml. of mesitylene containing 10.5 ml. of formic acid was heated under reflux for sixteen hours, cooled, basified with ammonium hydroxide, diluted with 100 ml. of water and extracted three times with diethyl ether. The combined ether extracts, on washing with water, drying and evaporation to dryness, afforded a residue which was steam distilled. The pot residue remaining after steam distillation was extracted with diethyl ether, and the combined ether extracts were washed once with water, once with saturated brine, dried and evaporated to dryness in vacuo to give 10.3 g. of a syrup. The latter was crystallized from ethanol to give 1.1 g. of 3,6(eq),11(ax)-trimethyl-11(eq) [-3-oxo-3-(2-furyl)propyl]-1,2,3,4,5,6-hexahydro-2,6-methano-3-benzazocine, m.p. 96°–98° C.

EXAMPLE 4

A solution of 1.0 g. (0.002 mole) of ethyl 1,4aα,5α-trimethyl-3-[β-(2-furyl)propionyl]-1,2,3,4,4a,5,10,10a-octahydro-2,5-methanobenzo[g]quinoline-3-carboxylate in 10 ml. of trimethylammonium formate was heated under reflux for ten minutes, and the mixture cooled and worked up as in Example 1. There was thus obtained 0.7 g. of crude product in the form of the free base which was converted to the methanesulfonate and recrystallized from acetone to give 0.60 g. of 3,6(eq),1-1(ax)-trimethyl-11(eq)-[3-oxo-5-(2-furyl)pentyl]-1,2,3,4,5,6-hexahydro-2,6-methano-3-benzazocine methanesulfonate, m.p. 144°–149° C.

EXAMPLE 5

A solution of methyl β-[3,6(eq),11(ax)-trimethyl-8-hydroxy-1,2,3,4,5,6-hexahydro-2,6-methano-3-benzazocin-11(eq)-yl]propionate ethanesulfonate (m.p. 268°–270° C. prepared from the corresponding 8-hydroxy compound and methanol using the procedure described above in Example 2), 50 ml. of dimethoxymethane and 0.5 ml. of ethanesulfonic acid in 100 ml. of methylene dichloride was heated under reflux under a Soxhlet extractor containing 4A molecular sieves. After refluxing for about twenty hours, an additional 20 ml. of dimethoxymethane was added, and refluxing was continued for another twenty-four hours. The mixture was then poured into an ice/dilute sodium hydroxide mixture and the mixture extracted with methylene dichloride. The extracts, after workup in the usual manner, afforded an oil which was dissolved in diethyl ether and treated with a molar excess of ethanesulfonic acid in diethyl ether. The solid which separated was collected, dried and recrystallized from acetone/diethyl ether to give 2.0 g. of methyl β-[3,6(eq),11(ax)-trimethyl-8-methoxymethoxy-1,2,3,4,5,6-hexahydro-2,6-methano-3-benzazocin-11(eq)-yl]propionate ethanesulfonate, m.p. 157°–159° C.

The latter (7.3 g., 0.020 mole) dissolved in 50 ml. of tetrahydrofuran was added to a stirred suspension of lithium diisopropylamide in 50 ml. of tetrahydrofuran, and the mixture was stirred at $-70°$ C. for one hour. The mixture was then treated with a solution of β-(3-furyl)propionyl chloride in 50 ml. of tetrahydrofuran over a period of one minute, and the mixture stirred at ambient temperature for about thirty minutes and then poured into 100 ml. of aqueous sodium bicarbonate. Extraction of the mixture with diethyl ether and isolation of the product from the ether solution afforded 14 g. of methyl β-[3,6(eq),11(ax)-trimethyl-8-methoxymethoxy-1,2,3,4,5,6-hexahydro-2,6-methano-3-benzazocin-11(eq)-yl]-α-[β-(3-furyl)propionyl]propionate as an oil.

The latter was dissolved in 55 ml. of trimethylammonium formate, the solution was boiled for 15 minutes, and the reaction mixture worked up in the manner described above in Example 2, the product being isolated in the form of the methanesulfonate salt, which was recrystallized from acetone to give 2.5 g. of 3,6(eq),1-1(ax)-trimethyl-8-hydroxy-11(eq)[3-oxo-5-(3-furyl)pentyl]-1,2,3,4,5,6-hexahydro-2,6-methano-3-benzazocine methanesulfonate, m.p. 206°–207° C.

EXAMPLE 6

Following a procedure similar to that described in Examples 1, 2 and 3, it is contemplated that the following compounds of formula I can also be prepared:

A. Reaction of ethyl 1,5α-dimethyl-7-methoxy-1,2,3,4,4a,5,10,10a-octahydro-2,5-methanobenzo[g]quinoline-3-carboxylate with β-(2-furyl)propionyl chloride in the presence of lithium diisopropylamide affords ethyl 1,5α-dimethyl-3-[β-(2-furyl)propionyl]-7-methoxy-1,2,3,4,4a,5,10,10a-octahydro-2,6-methanobenzo[g]quinoline-3-carboxylate which, on heating with trimethylammonium formate, affords 3,6(eq)-dimethyl-8-methoxy-11(eq)-[3-oxo-5-(2-furyl)pentyl]-1,2,3,4,5,6-hexahydro-2,6-methano-3-benzazocine.

B. Reaction of ethyl 1,4aα-dimethyl-6-methoxy-1,2,3,4,4a,5,10,10a-octahydro-2,5-methanobenzo[g]quinoline-3-carboxylate with 2-furoyl chloride in the presence of lithium diisopropylamide affords ethyl 1,4aα-dimethyl-3-(2-furoyl)-6-methoxy-1,2,3,4,4a,5,10,10a-octahydro-2,5-methanobenzo[g]quinoline-3-carboxylate which, on heating with trimethylammonium formate, affords 3,11(ax)-dimethyl-7-methoxy-11(eq)-[3-oxo-3-(2-furyl)propyl]-1,2,3,4,5,6-hexahydro-2,6-methano-3-benzazocine.

C. Reaction of ethyl 1,4aα,5α-trimethyl-8-methoxy-1,2,3,4,4a,5,10,10a-octahydro-2,5-methanobenzo[g]quinoline-3-carboxylate with 2-furoyl chloride in the presence of lithium diisopropylamide affords ethyl 1,4aα,5α-trimethyl-3-(2-furoyl)-8-methoxy-1,2,3,4,4,a,5,10,10a-octahydro-2,5-methanobenzo[g]quinoline-3-carboxylate which, on heating with trimethylammonium formate, affords 3,6(eq),11(ax)-trimethyl-9-methoxy-11(eq)-[3-oxo-3-(2-furyl)propyl]-1,2,3,4,5,6-hexahydro-2,6-methano-3-benzazocine.

D. Reaction of ethyl 1,4aα,5α-trimethyl-9-methoxy-1,2,3,4,4a,5,10,10a-octahydro-2,5-methanobenzo[g]quinoline-3-carboxylate with 2-furoyl chloride in the presence of lithium diisopropylamide affords ethyl 1,4aα,5α-trimethyl-3-(2-furoyl)-9-methoxy-1,2,3,4,4a,5,10,10a-octahydro-2,5-methanobenzo[g]quinoline-3-carboxylate which, on heating with trimethylammonium formate, affords 3,6(eq),11(ax)-trimethyl-10-methoxy-11(eq)-[3-oxo-3-(2-furyl)propyl]-1,2,3,4,5,6-hexahydro-2,6-methano-3-benzazocine.

E. Reaction of ethyl 1,4aα,5α-trimethyl-7-methoxy-1,2,3,4,4a,5,10,10a-octahydro-2,5-methanobenzo[g]quinoline-3-carboxylate with β-(3-furyl)propionyl chloride in the presence of lithium diisopropylamide affords ethyl 1,4aα,5α-trimethyl-3-[β-(3-furyl)propionyl]-7-methoxy-1,2,3,4,4a,5,10,10a-octahydro-2,5-methanobenzo[g]-quinoline-3-carboxylate which, on heating with trimethylammonium formate, affords 3,6(eq),11(ax)-trimethyl-8-methoxy-11(eq)-[3-oxo-5-(3-furyl)pentyl]-1,2,3,4,5,6-hexahydro-2,6-methano-3-benzazocine.

F. Reaction of ethyl 1,4aα,5α-trimethyl-7-methoxy-1,2,3,4,4a,5,10,10a-octahydro-2,5-methanobenzo[g]quinoline-3-carboxylate with β-(5-methyl-3-furyl)propionyl chloride in the presence of lithium diisopropylamide affords ethyl 1,4aα,5α-trimethyl-3-[β-(5-methyl-3-furyl)propionyl]-7-methoxy-1,2,3,4,4a,5,10,10a-octahydro-2,6-methanobenzo[g]quinoline-3-carboxylate which, on heating with trimethylammonium formate, affords 3,6(eq),11(ax)-trimethyl-8-methoxy-11(eq)-[3oxo-5-(5-methyl-3-furyl)pentyl]-1,2,3,4,5,6-hexahydro-2,6-methano-3-benzazocine.

G. Reaction of ethyl 1-methyl-4aα,5α-trimethylene-7-methoxy-1,2,3,4,4a,5,10,10a-octahydro-2,5-methanobenzo[g]quinoline-3-carboxylate with 2-furoyl chloride in the presence of lithium diisopropylamide affords ethyl 1-methyl-4aα,5α-trimethylene-3-(2-furoyl)-7-methoxy-1,2,3,4,4a,5,10,10a-octahydro-2,5-methanobenzo[g]quinoline-3-carboxylate which, on heating with trimethylammonium formate, affords 3-methyl-6(eq),11(ax)-trimethylene-8-methoxy-11(eq)-[3-oxo-3-(2-furyl)propyl]-1,2,3,4,5,6-hexahydro-2,6-methano-3-benzazocine.

H. Reaction of ethyl 1-methyl-4aα,5α-tetramethylene-7-methoxy-1,2,3,4,4a,5,10,10a-octahydro-2,5-methanobenzo[g]quinoline-3-carboxylate with 2-furoyl chloride in the presence of lithium diisopropylamide affords ethyl 1-methyl-4aα,5α-tetramethylene-3-(2-furoyl)-7-methoxy-1,2,3,4,4a,5,10,10a-octahydro-2,5-methanobenzo[g]quinoline-3-carboxylate which, on heating with trimethylammonium formate, affords 3-methyl-6(eq),11(ax)-tetramethylene-8-methoxy-11(eq)-[3-oxo-3-(2-furyl)propyl]1,2,3,4,5,6-hexahydro-2,6-methano-3-benzazocine.

EXAMPLE 7

A. Following a procedure similar to that described in Example 1, it is contemplated that by heating ethyl 9-methoxy-4aα,5α-dimethyl-3-[3-(3-furyl)-1-oxopropyl]1,2,3,4,4a,5,10,10a-octahydro-2,5-methanobenzo[g]quinoline-3-carboxylate with trimethylammonium formate, there can be obtained 6(eq),11(ax)-dimethyl-10-methoxy-11(eq)-[3-oxo-5-(3-furyl)pentyl]-1,2,3,4,5,6-hexahydro-2,6-methano-3-benzazocine.

B. Reaction of the latter with a molar equivalent amount of cyclopropylmethyl bromide, 2-phenylethyl bromide, allyl bromide or propargyl bromide affords, respectively, 3-cyclopropylmethyl-6(eq),11(ax)-dimethyl-10-methoxy-11(eq)-[3-oxo-5-(3-furyl)pentyl]-1,2,3,4,5,6-hexahydro-2,6-methano-3-benzazocine; 3-(2-phenylethyl)-6(eq),11(ax)-dimethyl-10-methoxy-11(eq)-[3-oxo-5-(3-furyl)pentyl]-1,2,3,4,5,6-hexahydro-2,6-methano-3-benzazocine; 3-(3-propen-1-yl)-6(eq),11(ax)-dimethyl-10-methoxy-11(eq)-[3-oxo-5-(3-furyl)pentyl]-1,2,3,4,5,6-hexahydro-2,6-methano-3-benzazocine or 3-(3-propyn-1-yl)-6(eq),11(ax)-dimethyl-10-methoxy- 11(eq)-[3-oxo-5-(3-furyl)pentyl]-1,2,3,4,5,6-hexahydro-2,6-methano-3-benzazocine.

EXAMPLE 8

It is contemplated that by refluxing a solution of 3,6(eq),11(ax)-trimethyl-8-hydroxy-11(eq)-[3-oxo-4-(2-furyl)butyl]-1,2,3,4,5,6-hexahydro-2,6-methano-3-benzazocine described above in Example 2 with a molar excess of dimethoxymethane in methylene dichloride in the presence of a catalytic amount of ethanesulfonic acid under a Soxhlet extractor containing 4A molecular sieves and isolation of the product from a neutral medium, there can be obtained 3,6(eq),11(ax)-trimethyl-8-methoxymethoxy-11(eq)-[3-oxo-4-(2-furyl)butyl]-1,2,3,4,5,6-hexahydro-2,6-methano-3-benzazocine.

BIOLOGICAL TEST RESULTS

The compounds of formula I are generally active in the acetylcholine-induced abdominal constriction test (Ach), a primary analgesic screening test, and also in the rat trail flick radiant thermal heat analgesic test (Tail Flick Agonist, T. F. Ag.) and also in the Straub tail test (Straub). Individual species have been found active in the phenazocine tail flick antagonist test (Phen.) indicating activity of these latter species as analgesic antagonists. Data so obtained for the compounds, identified by reference to the preceding examples and expressed either in terms of the ED$_{50}$ (mg./kg., subcutaneous administration) or in terms of percent inhibition, are given below. All doses are expressed in milligrams per kilogram (mg./kg.). The letter "I" means inactive at the indicated dosage.

| Example | Ach | Phen. | T.F. Ag. | Straub |
|---------|-------|-----------|-----------|--------|
| 1 | 0.050 | I/0.0-10 | 0.39 | 2.5 |
| 2 | 0.069 | 1.4 | 71%/240 43%/120 | 1.0 |
| 3 | 0.13 | I/0.1-0.01 | 0.66 | 1.0 |

We claim:
1. A compound having the formula

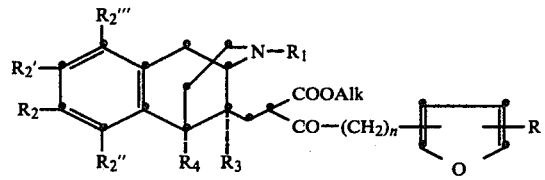

where R is hydrogen or lower-alkyl; $R_1$ is hydrogen, lower-alkyl, cyclo-lower-alkyl-lower-alkyl, phenyl-lower-alkyl, lower-alkenyl or lower-alkynyl; $R_2$, $R_2'$, $R_2''$ and $R_2'''$ are each hydrogen, or three of them are hydrogen and the fourth is hydroxy, methoxymethoxy, lower-alkoxy or 2-tetrahydropyranyloxy; $R_3$ and $R_4$ are each hydrogen or lower-alkyl, or $R_3$ and $R_4$ together are divalent lower-alkylene, —$(CH_2)_m$—, where m is one of the integers 3 and 4; n is one of the integers 1 and 2; and Alk is lower-alkyl.

2. A compound according to claim 1 where R, $R_2'$, $R_2''$ and $R_2'''$ are each hydrogen; $R_1$, $R_3$ and $R_4$ are each lower-alkyl; and $R_2$ is methoxymethoxy.

3. Methyl β-[3,6(eq),11(ax)-trimethyl-8-methoxymethoxy-1,2,3,4,5,6-hexahydro-2,6-methano-3-benzazocin-11(eq)-yl]-α-[β-(3-furyl)propionyl]propionate according to claim 2.

* * * * *

UNITED STATES PATENT AND TRADEMARK OFFICE
CERTIFICATE OF CORRECTION

PATENT NO. : 4,228,286
DATED : October 14, 1980
INVENTOR(S) : Thomas R. Lewis and William F. Michne It is certified that error appears in the above-identified patent and that said Letters Patent are hereby corrected as shown below:

Column 2, line 4, change "erms" to read --terms--.

Column 2, line 34, change "...$R_2''R_2'''$....." to read --$R_2''$, $R_2'''$.....--.

Column 3, line 59, change "compound" to read --compounds--.

Column 4, line 33, change "4,148,749" to read --4,148,794--.

Column 6, line 8, change "analgestic" to read --analgesic--.

Signed and Sealed this

Sixteenth Day of November 1982

[SEAL]

Attest:

Attesting Officer

GERALD J. MOSSINGHOFF
Commissioner of Patents and Trademarks